US00PP26763P3

(12) United States Plant Patent
Contreras et al.

(10) Patent No.: US PP26,763 P3
(45) Date of Patent: May 31, 2016

(54) FLOWERING CURRANT PLANT NAMED 'OREGON SNOWFLAKE'

(50) Latin Name: *Ribes sanguineum*
Varietal Denomination: Oregon Snowflake

(71) Applicant: Oregon State University, Corvallis, OR (US)

(72) Inventors: Ryan N. Contreras, Corvallis, OR (US); Mara Wynne Friddle, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 119 days.

(21) Appl. No.: 14/121,395

(22) Filed: Aug. 29, 2014

(65) Prior Publication Data

US 2016/0066486 P1 Mar. 3, 2016

(51) Int. Cl.
*A01H 5/02* (2006.01)

(52) U.S. Cl.
USPC ..... Plt./156

(58) Field of Classification Search
USPC ..... Plt./156
See application file for complete search history.

(56) References Cited

PUBLICATIONS

Kim et al. EMS mutagenesis of Arabidopsis Methods in Molecular Biology vol. 323 Second edition 2006.*
http://www.oregonlive.com/hg/index.ssf/2014/05/new_oregon_snowflake_shrub_is.html.*

* cited by examiner

*Primary Examiner* — Annette Para
(74) *Attorney, Agent, or Firm* — Klarquist Sparkman, LLP

(57) ABSTRACT

A new cultivar of *Ribes sanguineum*, 'Oregon Snowflake', characterized by its compact and densely branched growth habit and highly dissected leaves.

3 Drawing Sheets

Botanical classification: *Ribes sanguineum.*
Cultivar designation: 'Oregon Snowflake'.

BACKGROUND OF THE INVENTION

The present invention relates to a new and distinct cultivar of *Ribes sanguineum* named 'Oregon Snowflake' and is hereinafter referred to by the cultivar name 'Oregon Snowflake'. 'Oregon Snowflake' represents a new cultivar of flowering currant characterized by its compact and densely branched growth habit and highly dissected leaves.

This new cultivar of flowering currant was developed by the Oregon State University Breeding Program (Corvallis, Oreg.). 'Oregon Snowflake' was selected by the Inventors in 2011 as accession OSU-11-0020-48-0-052 from a population of plants that were part of a mutation breeding program designed to induce variation in morphology. From a population of approximately 300 surviving plants grown in a greenhouse, 'Oregon Snowflake' was selected based on uniqueness and highly dissected leaf morphology. Rooted cutting (clones) were grown and plants were planted in a replicated, non-randomized trial as plants 13-01 (mother plant), 13-02, 13-03, 13-04, 13-05, and 13-06 in 2012 at the Lewis-Brown Horticultural Research Farm in Corvallis, Oreg. Plants have been repeatedly propagated via stem cuttings and it roots readily from terminal softwood cuttings treated with a basal dip of 1,000 ppm aqueous solution of indole butyric acid potassium salt. We have observed at least 80% rooting percentage of terminal cuttings but approximately 45% of non-terminal lateral stem cuttings.

'Oregon Snowflake' has been observed to retain its characteristics through multiple years of container (4 years), and field growing (3 years), as well as successive asexual propagations via stem cuttings under the direction of the Inventors at the Lewis-Brown Horticultural Research Farm in Corvallis, Oreg. Asexual reproduction of the new cultivar has shown that the unique features are stable and reproduced true to type in successive generations. An herbarium voucher was prepared and deposited into the Oregon State University Herbarium and is cataloged as accession OSC-240116.

SUMMARY OF THE INVENTION

The following traits have been repeatedly observed and represent the characteristics of the new cultivar. These attributes in combination distinguish 'Oregon Snowflake' as a new and unique cultivar of *Ribes sanguineum.*

1. 'Oregon Snowflake' exhibits highly dissected leaves.
2. 'Oregon Snowflake' exhibits compact, rounded habit with dense branching.

Figure 1:
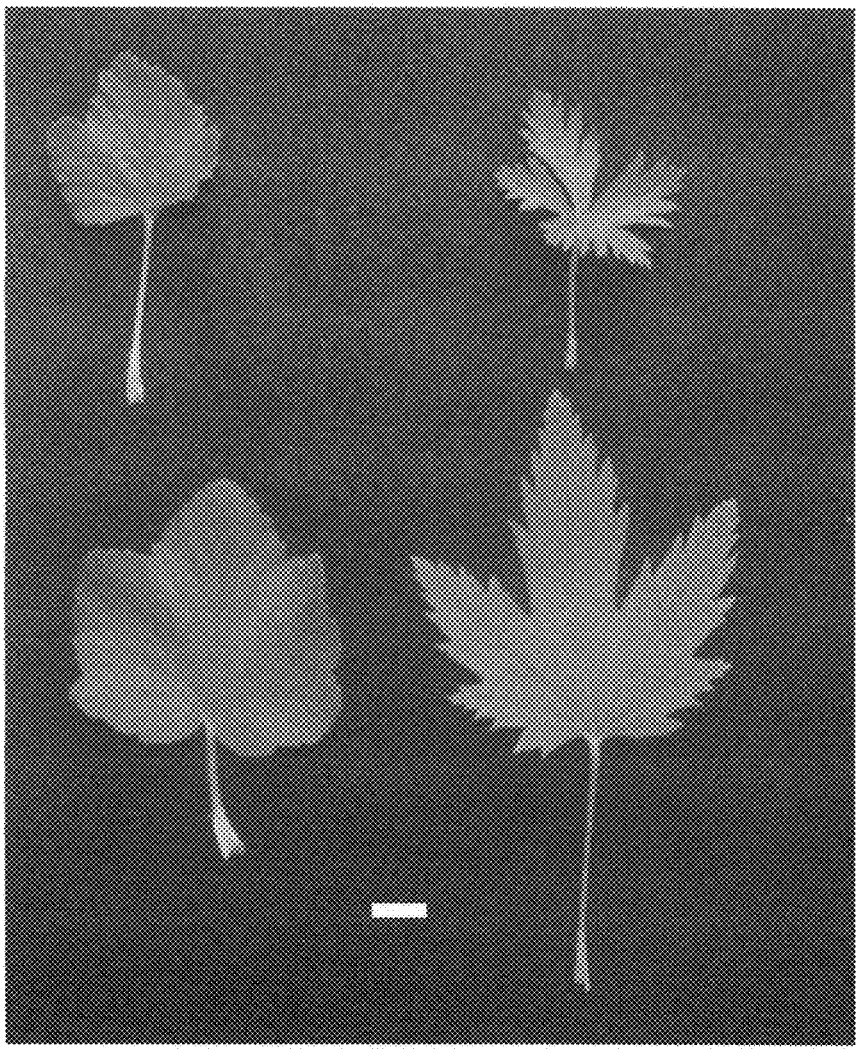

Table 1 shows the differences between 'Oregon Snowflake' and commercial variety 'White Icicle' (unpatented). We selected 'White Icicle' for comparison because it is the most commonly grown white flowering selection in the nursery trade. FIG. 1 also shows the differences in leaf size and shape between 'Oregon Snowflake' and 'White Icicle'. As shown in Table 1 and FIG. 1, 'Oregon Snowflake' is distinguished from 'White Icicle' based on increased dissection and differently shaped leaves as well as a more compact and rounded growth habit, which is wider than tall in 'Oregon Snowflake', as opposed to the more upright 'White Icicle'.

TABLE 1

Comparison of 'Oregon Snowflake' to 'White Icicle', a commercial variety.

| Trait | Variety | |
|---|---|---|
| | 'Oregon Snowflake' | 'White Icicle' |
| Mature height[1] | 121 cm | 154 cm |
| Mature width | 133 cm | 115 cm |
| Growth habit | Densely branched, semi-dwarf; low, mounded shape | Upright, ascending branches; few lateral branches |
| Leaf shape | Palmatifid with 5 lobes, deep lobes serrate-incised shallow sinuses; | Rounded lobes (5) with sinuses; crenate-serrate |
| Leaf length with petiole | 92.8 mm | 53.3 mm |
| Leaf blade length | 50.6 mm | 36.7 mm |
| Leaf width | 52.6 mm | 53.4 mm |

[1]Oregon Snowflake' measurement collected on Mar. 20, 2014 from original plant that was planted in spring 2012 as a #3 container grown plant. 'White Icicle' measurement collected on Mar. 20, 2014 from a plant that was planted spring 2013 as a #3 container grown plant. Ultimate height of 'White Icicle' likely underestimated by this measurement.

Table 2 shows the height differences between 'Oregon Snowflake' and other plants grown from the same seed treated with no EMS or 0.2% EMS, as well as other flowering currant plants. As shown in Table 2 and FIGS. 2-3, 'Oregon Snowflake' can be distinguished from other flowering currant plants based on its shorter height.

TABLE 2

Comparison of mean plant height of populations of plants treated with varying EMS rates and durations with 'Oregon Snowflake' and four industry standard cultivars.

| Cultivar | EMS rate (%) | Treatment duration | Mean height (cm) |
|---|---|---|---|
| | 0[z] | 24 | 183.8 ± 6.4 |
| | 0[z] | 48 | 186.4 ± 7.6 |
| | 0.2 | 24 | 184.6 ± 2.3 |
| | 0.2 | 48 | 159 ± 19.6 |
| 'Oregon Snowflake' | | | 112.3 ± 9 |
| 'King Edward VII' | | | 216.7 ± 4.4 |
| 'Pokey's Pink' | | | 176.7 ± 14.8 |
| 'Pulborough Scarlet' | | | 205.7 ± 14.5 |
| 'White Icicle' | | | 213.3 ± 9 |

[z]Control plants receiving no EMS.

BRIEF DESCRIPTION OF THE PHOTOGRAPHS

The accompanying colored photographs illustrate the overall appearance and distinct characteristics of the new *Ribes* cultivar.

The photograph in FIG. 1 provides a leaf comparison of 'White Icicle' (right column) and 'Oregon Snowflake' (left column). Immature leaves are shown on the upper panels, mature leaves are shown on the lower panels (Scale=1 cm).

Figure 2:
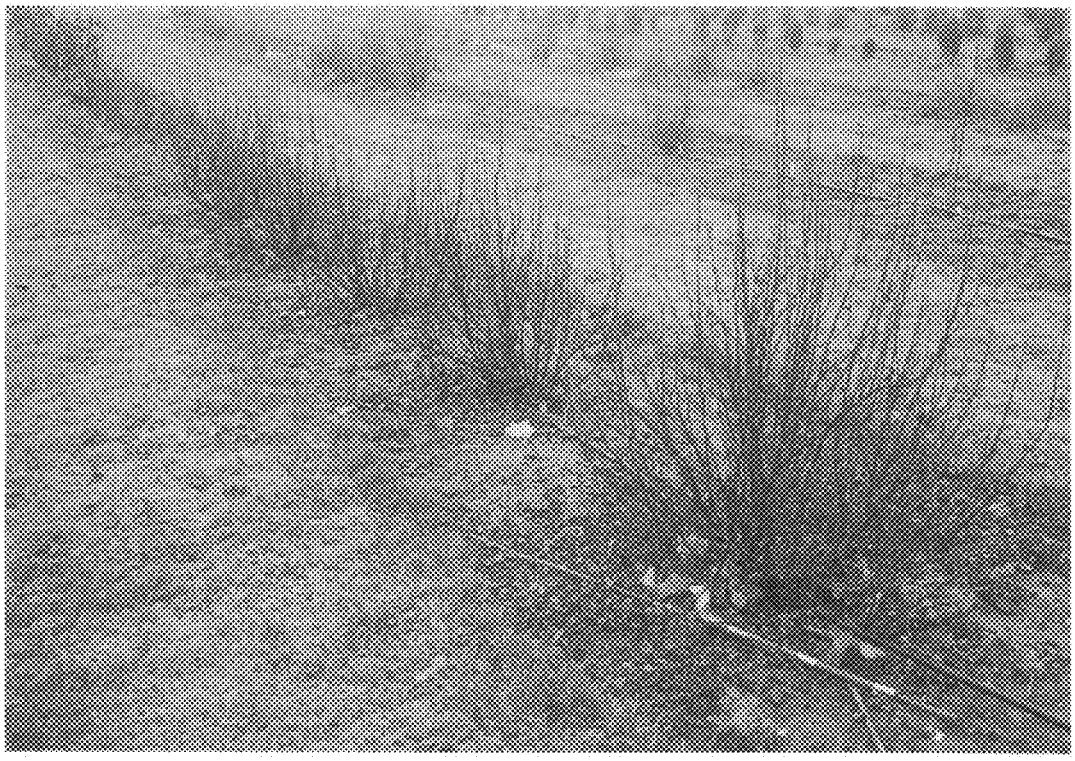

The photograph in FIG. 2 provides a close-up view of the 'Oregon Snowflake' cultivar during winter with its characteristic dense branching. The photo show the mother plant in the foreground with five (5) replicates planted thereafter, demonstrating growth habit consistency in plants propagated asexually from stem cuttings. These plants were approximately 2.5 years old at the time the photographs were taken and are located at the Lewis-Brown Horticulture Research Farm at 33329 Peoria Rd. Corvallis, Oreg. 97333.

Figure 3:
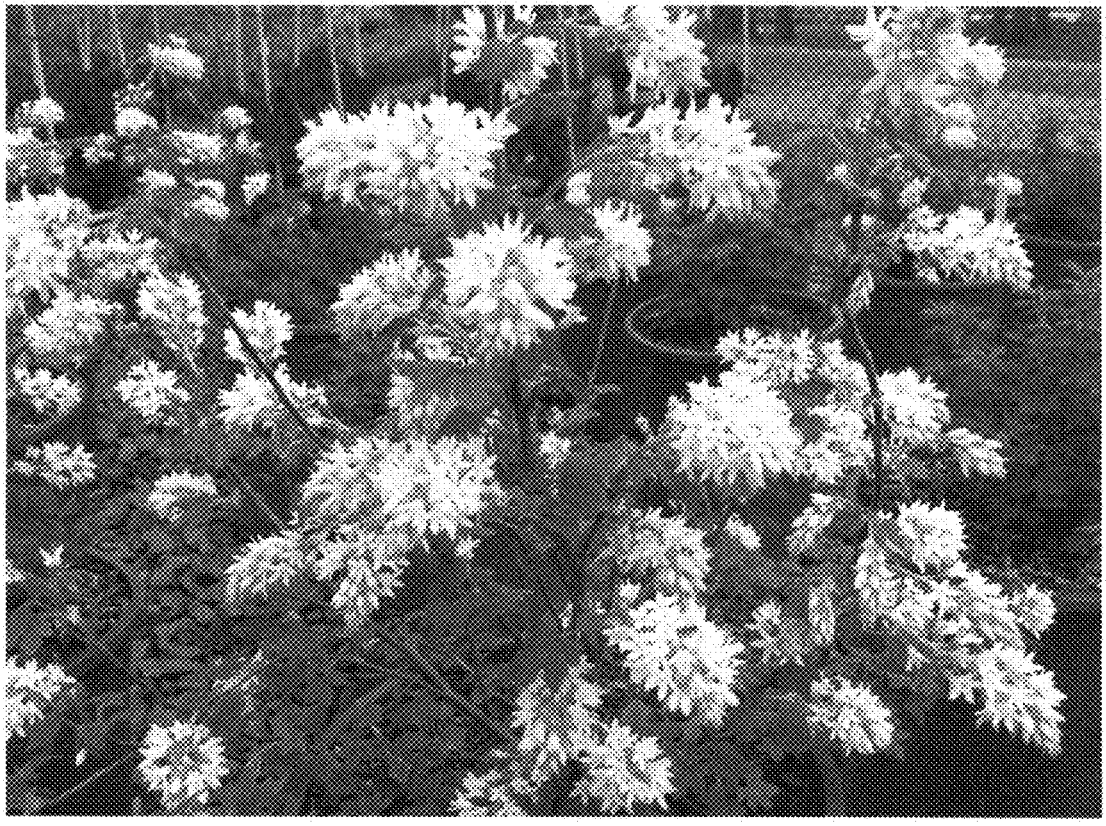

The photograph in FIG. 3 provides a close-up view of 'Oregon Snowflake' in full flower.

DETAILED BOTANICAL DESCRIPTION OF THE PLANT

The following detailed description sets forth the distinctive characteristics of 'Oregon Snowflake'. The detailed description was taken from plants that had been growing for two years at the Lewis-Brown Horticultural Research Farm, Corvallis, Oreg. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Parentage: Seed (non-patented) purchased from Seven Oaks Native Nursery, Albany, Oreg. was treated with ethylmethane sulfonate (EMS). Lots of 500 seed were immersed in 50 mL each of 0, 0.2, 0.4, 0.8, and 1.2% EMS in a 0.1 M sodium phosphate buffer. There were three replicates of each treatment and 24- and 48-h durations of each treatment. All seed were then triple-rinsed for 15 minutes in Millipore water and put into cold stratification at 36-38° F. for 6 weeks. Seed were sown on a 1:1 mix of Sunshine potting mix SB40 (Sun Gro Horticulture, Belvue, Wash.) and douglas-fir bark mulch in 10"×20" flats.

General description:

*Plant type*.—Deciduous shrub.

*Plant habit*.—Compact, rounded, and densely branched. Semi-dwarf.

*Height and spread*.—Average height of 1.21 m and average width of 1.33 at maturity.

*Cold hardiness*.—USDA Zone (5)6.

*Disease and pests*.—Comparable to 'White Icicle'.

*Culture*.—Plants prefer moist, well-drained soil in full sun or partial shade. Tolerates moderate drought.

*Propagation*.—Roots easily from terminal stem cuttings treated with auxin and placed under intermittent mist.

*Growth rate*.—4 to 5 feet in three years with an average height of just under 4 feet (1.21 m).

Stem description:

*Stem*.—Appears glabrous but under magnification is sparsely tomentulose. One (1) -year old stems are 164A in color on lower portion of stem growth, 167B in color in the middle of stem growth, and 174A in color on the upper, newer portion of stem growth.

*Internodes*.—Mean length 1.1 cm.

Foliage description:

*Leaf shape*.—Palmatifid with five lobes and very deep sinuses; lobes serrate-incised.

*Leaf division*.—Simple leaves.

*Leaf base*.—Cordate.

*Leaf apex*.—Serrate-incised lobes.

*Leaf venation*.—Impressed adaxially.

*Leaf margins*.—Serrate-incised with glandular hairs.

*Leaf attachment*.—Petiolate.

*Leaf arrangement*.—Alternate.

*Leaf surface* (*mature*).—Sparsely velutinous with surface glands; glandular hairs marginally.

*Leaf surface* (*immature*).—Plicate, adaxially velutinous with glandular hairs marginally; abaxially velutinous and glandular mixture of hairs.

*Leaf color* (*mature*).—Adaxial surface is 137B in color; abaxial surface is 139C in color.

*Leaf color* (*immature*).—Adaxial surface is 137B in color; abaxial surface is 137D in color.

*Leaf size* (*mature*).—Length including petiole=92.8 mm; blade length=50.6 mm; width=52.6 mm.

*Petioles*.—Involute in shape (ridge on adaxial surface), an average of 26 mm in length and 1.1 mm in width, surface is velutinous with sparse glandular hairs.

*Stipules*.—Generally reduced to adnate sheath at the base of the petiole.

Inflorescence description:

*Type*.—Raceme.

*Habit*.—Pendulous.

*Bloom season*.—Spring, mid-March to mid-April in Corvallis, Oreg.

*Pedicels*.—8.66 mm.

*Peduncles*.—38.6 mm.

*Number of flowers per inflorescence*.—Thirty nine (39).

*Fragrance*.—No floral fragrance but entire plant has spicy fragrance typical of the species.

*Length at anthesis*.—102.8 mm.

*Self cleaning or persistent*.—Semi-self cleaning.

*Flower buds*.—Glabrous with glandular hairs marginally; falcate with four scales oppositely arranged; length is 13.1 mm.

*Flowers*.—Tubular; outer is 157D in color and pedicel to tip is 19.7 mm.

*Perianth*.—Length=9.4 mm; Width=13.7 mm.

*Sepals*.—Five (5) sepals fused; calyx tube=5.9 mm; calyx lobes=7.1 mm.

*Petals*.—Reduced petals, five (5), fused to interior calyx wall; minute; 157D in color.

*Fruit*.—Bluish-black with glaucous, waxy bloom.

*Bracts*.—Single Bracteole, persistent; glandular with sparse velutinous pubescence; 145B in color.

Reproductive organs:

*Stamen*.—Five (5) per flower; 3.7 mm in length.

*Pistil*.—One (1) per flower with two (2) to three (3) stigmas; 6.9 mm in length.

*Ovary*.—Inferior; 149A in color.

It is claimed:

1. A new and distinct cultivar of flowering currant plant named 'Oregon Snowflake' as herein illustrated and described.

* * * * *